United States Patent
Rottenberg (10) Patent No.: US 10,514,333 B2
(45) Date of Patent: Dec. 24, 2019

(54) ABSORPTION SPECTRUM DETECTION OF A FLUID

(71) Applicant: IMEC VZW, Leuven (BE)

(72) Inventor: Xavier Rottenberg, Kessel-Lo (BE)

(73) Assignee: IMEC VZW, Leuven (BE)

( * ) Notice: Subject to any disclaimer, the term of this patent is extended or adjusted under 35 U.S.C. 154(b) by 3 days.

(21) Appl. No.: 15/735,475

(22) PCT Filed: Jun. 30, 2016

(86) PCT No.: PCT/EP2016/065314
§ 371 (c)(1),
(2) Date: Dec. 11, 2017

(87) PCT Pub. No.: WO2017/001566
PCT Pub. Date: Jan. 5, 2017

(65) Prior Publication Data
US 2018/0156716 A1 Jun. 7, 2018

(30) Foreign Application Priority Data
Jun. 30, 2015 (EP) ..................... 15174688

(51) Int. Cl.
*G01N 21/31* (2006.01)
*G01N 21/03* (2006.01)
*B01L 3/00* (2006.01)

(52) U.S. Cl.
CPC .... *G01N 21/0303* (2013.01); *B01L 3/502715* (2013.01); *G01N 21/03* (2013.01);
(Continued)

(58) Field of Classification Search
CPC ............ B01L 3/502715; G01N 21/31–21/314
See application file for complete search history.

(56) References Cited

U.S. PATENT DOCUMENTS

| | | | | |
|---|---|---|---|---|
| 5,444,807 A | * | 8/1995 | Liu | .............. G01N 30/74 204/452 |
| 7,186,567 B1 | | 3/2007 | Sutherland et al. | |

(Continued)

FOREIGN PATENT DOCUMENTS

| | | |
|---|---|---|
| CN | 104655566 A | 5/2015 |
| EP | 2 913 663 A1 | 9/2015 |

(Continued)

OTHER PUBLICATIONS

PCT International Search Report and Written Opinion; PCT International Application No. PCT/EP2016/065314, dated Oct. 10, 2016, 14 pages.
(Continued)

*Primary Examiner* — Rebecca C Bryant
(74) *Attorney, Agent, or Firm* — McDonnell Boehnen Hulbert & Berghoff LLP (57) ABSTRACT

The present disclosure describes a device for measuring an optical absorption property of a fluid as function of wavelength. The device comprises a broadband light source for emitting light, a plurality of integrated optical waveguides for guiding this light and a light coupler for coupling the emitted light into the integrated optical waveguides such that the light coupled into each integrated optical waveguide has substantially the same spectral distribution. The device also comprises a microfluidic channel for containing the fluid, arranged such as to allow an interaction of the light propagating through each waveguide with the fluid in the microfluidic channel, and a plurality of spectral analysis devices optically coupled to corresponding waveguides—such as to receive the light after interaction with the fluid. The spectral analysis devices are adapted for generating a signal representative of a plurality of spectral components of the light.

21 Claims, 2 Drawing Sheets

(52) U.S. Cl.
CPC ........... *G01N 21/31* (2013.01); *G01N 21/314* (2013.01); *B01L 2300/0816* (2013.01); *B01L 2400/0406* (2013.01); *B01L 2400/0457* (2013.01); *B01L 2400/0487* (2013.01); *G01N 2021/0346* (2013.01); *G01N 2021/3137* (2013.01); *G01N 2021/3166* (2013.01); *G01N 2021/3181* (2013.01); *G01N 2201/062* (2013.01); *G01N 2201/066* (2013.01); *G01N 2201/0633* (2013.01); *G01N 2201/0636* (2013.01); *G01N 2201/0873* (2013.01)

(56) References Cited

U.S. PATENT DOCUMENTS

| | | | |
|---|---|---|---|
| 2006/0165342 | A1 | 7/2006 | Pau et al. |
| 2013/0005606 | A1 | 1/2013 | Chakravarty et al. |
| 2013/0261010 | A1* | 10/2013 | Bailey .................... G01N 27/72 506/9 |
| 2016/0356720 | A1* | 12/2016 | Van Dorpe .......... A61B 5/0066 |

FOREIGN PATENT DOCUMENTS

| | | | |
|---|---|---|---|
| WO | 2006/010367 | A2 | 2/2006 |
| WO | WO-2008122907 | A2 * | 10/2008 .............. F21V 11/02 |

OTHER PUBLICATIONS

Balslev, S. et al., "Fully Integrated Optical Systems for Lab-on-a-Chip Applications", Optical Sensing II, vol. 5730, Mar. 7, 2005, pp. 211-217.

Ryckeboer, E. et al., "Glucose Sensing by Waveguide-Based Absorption Spectroscopy on a Silicon Chip", Biomedical Optics Express, vol. 5, No. 5, Apr. 24, 2014, pp. 1636-1648.

* cited by examiner

ABSORPTION SPECTRUM DETECTION OF A FLUID

CROSS-REFERENCE TO RELATED APPLICATION

The present application is a national stage entry of PCT/EP2016/065314 filed Jun. 30, 2016, which claims priority to European Patent Application No. 15174688.0 filed Jun. 30, 2015, the contents of which are hereby incorporated by reference.

FIELD OF THE DISCLOSURE

The present disclosure relates to the field of measurements of optical absorption in fluids as function of wavelength, in integrated circuitry devices. More specifically it relates to a device for measuring an optical absorption property of a fluid as function of wavelength.

BACKGROUND

Integrated circuits are used for the measurement of optical absorption properties of fluids, such as gases or biological fluids, as function of wavelength, using integrated optical waveguides. The fluid being analyzed may for example be introduced in an integrated microfluidic channel that is arranged such as to allow an interaction with electromagnetic radiation propagating through an integrated waveguide structure, for example such structure in or on an integrated photonics substrate. These measurements may be used to obtain colorimetric information pertaining to a fluid sample. While few spectral data samples may be sufficient to characterize a target compound in the fluid sample in some applications, a high spectral resolution may be used to accurately characterize a fluid in many situations, e.g. to accurately determine a concentration of a target analyte. For example, while a transmission peak at a predetermined wavelength may be highly sensitive to the concentration of the target analyte in the sample, changes in absorption are often associated with wavelength shifts, such that a good spectral resolution may also be used in accurately determining the concentration.

Particularly, highly sensitive optical absorption measurements as function of wavelength, e.g. forming an absorption spectrum of sufficient spectral resolution for the intended purpose, may be used for detecting biological and/or chemical agents in the sample being analyzed, e.g. for the detection of target analytes such as proteins, antigens or antibodies. Applications of such measurements may include for example environmental monitoring, toxicology, medical diagnostics and gas sampling.

For example, a laser may be used as light source, e.g. a tunable laser or one or more lasers with corresponding predetermined laser emission spectra. The light emitted by the laser may be coupled into a waveguide, such as a slab waveguide or rib waveguide. The waveguide may have a section of a substantial length, which is arranged in close proximity to the material under test. The tested material may for example be introduced into a microfluidic channel that is arranged sufficiently close to this waveguide section such that an interaction of the light conducted in the waveguide can occur with the material in the microfluidic channel, e.g. an interaction of the evanescent field of the light.

For some tests, presence of light at different frequencies may be desired. However, the use of multiple lasers having different, predetermined spectra, the use of tuneable lasers or of broadband lasers can be expensive, and such sources may be difficult to integrate in an integrated optical device. Inexpensive wideband light sources are also known, such as light emitting diodes (LED). However, such inexpensive wide-band light sources may have a high etendue when coupled into an integrated waveguide. This high etendue may severely reduce the coupling efficiency.

SUMMARY

It is an object of embodiments of the present disclosure to provide good, inexpensive and/or efficient multi-spectral measurements, in an integrated device, of optical absorption properties of a fluid.

The above objective is accomplished by a method and device according to embodiments of the present disclosure.

In a first aspect, the present disclosure relates to a device for measuring an optical absorption property of a fluid as a function of wavelength. The device comprises a broadband light source for emitting light, a plurality of integrated optical waveguides for guiding this light and a light coupler for coupling the light emitted by the broadband light source into the plurality of integrated optical waveguides, such that the light coupled into each of the integrated optical waveguides has substantially the same spectral distribution, e.g. has the same spectral distribution. The device further comprises a microfluidic channel for containing the fluid. The microfluidic channel is arranged such as to allow an interaction of the light propagating through each of the integrated optical waveguides with the fluid when contained in the microfluidic channel. The device also comprises a plurality of spectral analysis devices. Each spectral analysis device is optically coupled to a corresponding integrated optical waveguide of the plurality of integrated optical waveguides, such as to, in operation, receive the light after the interaction of the light with the fluid. Each spectral analysis device is also adapted for generating a signal representative of a plurality of predetermined spectral components of the light.

In a device according to embodiments of the present disclosure, the light coupler may comprise a collimator for collimating the light emitted by the broadband light source into a collimated radiation beam. The light coupler may further comprise a beam shaper for distributing the power of the collimated light over a discrete number of line shaped light fields, in which this beam shaper is arranged such that each line shaped light field is projected onto a light entry surface of a corresponding waveguide of the plurality of integrated optical waveguides.

In a device according to embodiments of the present disclosure, the collimator may have a parabolic shape, a conic shape or a horn-like shape.

In a device according to embodiments of the present disclosure, the beam shaper may comprise a structured transparent slab comprising a plurality of light separating lamellae for reflecting light away from the lamellae and toward the nearest line shaped light field.

In a device according to embodiments of the present disclosure, the beam shaper may have a wedge shape. The collimator and the beam shaper may furthermore be arranged such that the beam shaper can receive light from the collimator via a wedge entrance area forming a short side of the wedge.

In a device according to embodiments of the present disclosure, the number of integrated optical waveguides in the plurality of integrated optical waveguides may be in the range of 100 to 10,000,000.

In a device according to embodiments of the present disclosure, each waveguide of the plurality of integrated optical waveguides may comprise a light receiving portion adapted for coupling the light emitted by the broadband light source into the waveguide. The light receiving portions of the plurality of integrated optical waveguides may furthermore be arranged substantially parallel with respect to each other.

In a device according to embodiments of the present disclosure, each waveguide of the plurality of integrated optical waveguides may be configured to keep the light traveling along different waveguides physically separate.

In a device according to embodiments of the present disclosure, at least one waveguide of the plurality of integrated optical waveguides may be curved in an interaction portion where the light propagating through the integrated optical waveguides can interact with the fluid when contained in the microfluidic channel.

In a device according to embodiments of the present disclosure, this interaction portion may be a curved section of the waveguide having an extrinsic curvature of at least the reciprocal of the diameter of the microfluidic channel.

In a device according to embodiments of the present disclosure, at least one waveguide of the plurality of integrated optical waveguides may have a spiral-like shape in the interaction portion.

In a device according to embodiments of the present disclosure, the broadband light source may have a substantially spherical or Lambertian spatial light emission distribution.

In a device according to embodiments of the present disclosure, the broadband light source may comprise a light emitting diode.

A device according to embodiments of the present disclosure may further comprise a signal combiner, e.g. a processing unit or processor, adapted for receiving the signal from the plurality of spectral analysis devices and for generating therefrom an aggregated signal representative of the absorption spectrum of the fluid.

In a device according to embodiments of the present disclosure, this signal combiner may furthermore be adapted for generating a signal indicative of a presence and/or a concentration of a predetermined target biological and/or chemical agent in the fluid.

In a second aspect, the present disclosure also relates to a method for measuring an optical absorption property of a fluid as a function of wavelength. This method comprises emitting light using a broadband light source, and coupling the emitted light into a plurality of integrated optical waveguides for guiding the light, e.g. using a light coupler. The emitted light is coupled into the plurality of integrated optical waveguides such that the light coupled into each integrated optical waveguide has substantially the same spectral distribution. The method further comprises bringing a fluid to be tested sufficiently close to each waveguide of the plurality of integrated optical waveguides such as to allow an interaction of the light propagating through each waveguide with the fluid. The method further comprises analyzing the spectrum of the light after the interaction of the light with the fluid, e.g. using a plurality of spectral analysis devices optically coupled to the corresponding integrated optical waveguides. The method also comprises generating a signal representative of a plurality of spectral components of the light.

A method according to embodiments of the present disclosure may also comprise providing the fluid in a microfluidic channel for containing the fluid that is arranged such as to allow an interaction of the light propagating through each waveguide with the fluid.

In a method according to embodiments of the present disclosure, analyzing the spectrum may comprise decomposing the light received from each of the plurality of waveguides after interaction with the fluid, into the same set of predetermined spectral components.

In a further aspect, the present disclosure may also relate to the use of a device according to embodiments of the present disclosure for the detection and/or quantification of biological and/or chemical agents in the fluid. The present disclosure may also relate to the use of a device according to embodiments of the present disclosure for the detection and/or quantification of target analytes such as proteins, antigens, or antibodies. The present disclosure may also relate to the use of a device according to embodiments of the present disclosure for environmental monitoring, toxicology, medical diagnostics, and/or gas sampling.

In example embodiments of the present disclosure, an inexpensive and readily available broadband light source, e.g. a LED, can be used in an integrated device for multi-spectral optical absorption measurement.

In example embodiments of the present disclosure, a high coupling efficiency can be achieved of light from a broadband light source, such as a LED, into an integrated waveguide structure in an integrated device for multi-spectral absorption measurement.

In example embodiments of the present disclosure, an overall high etendue acceptance can be achieved in an integrated device for multi-spectral absorption measurement for light emitted by a broadband light source.

Particular aspects of the disclosure are set out in the accompanying independent and dependent claims. Features from the dependent claims may be combined with features of the independent claims and with features of other dependent claims as appropriate and not merely as explicitly set out in the claims.

These and other aspects of the disclosure will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the disclosure.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed disclosure requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Where in embodiments of the present disclosure reference is made to "light", reference is made to electromagnetic radiation, e.g. composed of photon wave-particles that can be guided by an integrated waveguide structure in an integrated photonic circuit. This comprises, but is not necessarily limited to, visible light, e.g. electromagnetic radiation in a portion of the electromagnetic spectrum which is visible to the human eye. However, such light may also comprise electromagnetic radiation in a portion of the electromagnetic spectrum corresponding to, for example, infrared light, e.g. near-infrared light, and/or ultraviolet light. Where reference is made to broadband light, reference is made to light having a spectral distribution, e.g. a wavelength distribution of a substantially contiguous and/or continuous spectral component of the light, that has a full width at half maximum of at least 50 nm, at least 100 nm, or even wider, e.g. at least 200 nm or at least 300 nm.

In a first aspect, the present disclosure relates to a device for measuring an optical absorption property of a fluid as function of wavelength. The device comprises a broadband light source for emitting light, a plurality of integrated optical waveguides for guiding the light, and a light coupler for coupling the light emitted by the broadband light source into the plurality of integrated optical waveguides. The light coupler couples the light into the plurality of integrated optical waveguides such that the light coupled into each integrated optical waveguide has substantially the same spectral distribution. The device also comprises a microfluidic channel for containing the fluid, the microfluidic channel arranged such as to allow an interaction of the light propagating through each integrated optical waveguide with the fluid when contained in the microfluidic channel. The device further comprises a plurality of spectral analysis devices, each spectral analysis device being optically coupled to a corresponding integrated optical waveguide such as to, in operation, receive the light after the interaction of the light with the fluid. Each spectral analysis device is adapted for generating a signal representative of a plurality of spectral components of the light. The plurality of spectral components corresponding to the generated signal may be substantially the same for each pair of spectral analysis devices, e.g. each spectral analysis device may be adapted for decomposing the received light into the same set of spectral components.

Figure 1:
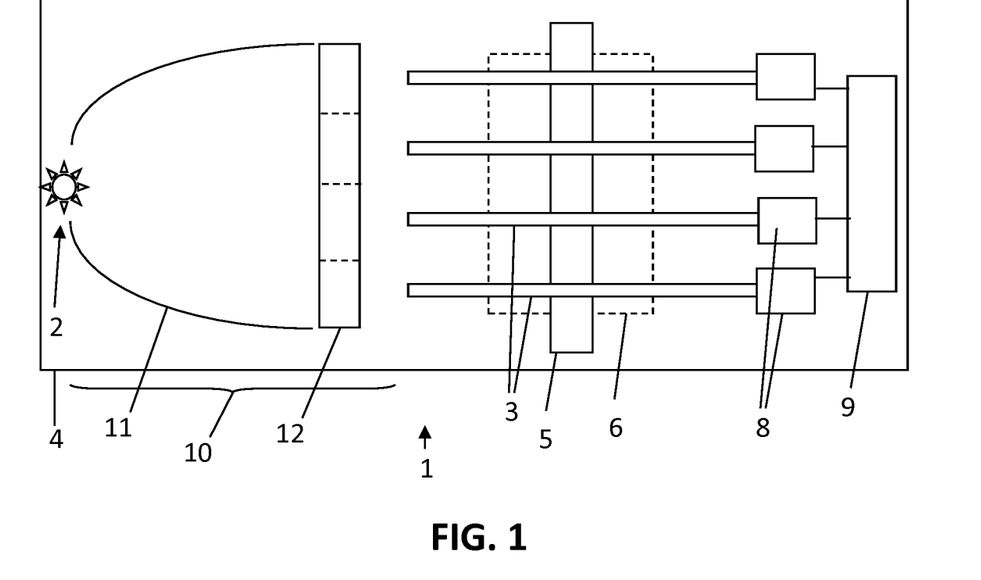
FIG. 1 shows a device in accordance with embodiments of the present disclosure.

An exemplary device 1 in accordance with embodiments of the present disclosure is shown in FIG. 1. The device 1 is adapted for measuring an optical absorption property of a fluid as a function of wavelength. The device 1 may be adapted for obtaining colorimetric information pertaining to the fluid. The device 1 may be adapted for performing optical absorption measurements as function of wavelength, e.g. for determining an absorption spectrum of the fluid at a substantial spectral resolution, e.g. comprising determined values indicative of at least 32, e.g. at least 64, or even at least 128, such as at least 256, or even a higher number, e.g. 1000 or more, substantially distinct spectral components of the absorption spectrum. The device may be adapted for detecting a biological and/or chemical agent in the sample being analyzed, e.g. for the detection of target analytes such as proteins, antigens, or antibodies. The device may be adapted for use in environmental monitoring, toxicology, medical diagnostics, and/or gas sampling.

The device comprises a broadband light source 2 for emitting light. This broadband light source 2 may comprise a light emitting diode (LED). This broadband light source 2 may have a predetermined light emission spectrum, e.g. a known and sufficiently stable spectrum suitable for use as a reference spectrum, such as to enable a measurement of a spectrum of the light after having interacted with the fluid to be tested, which spectrum is representative of absorption properties of the fluid. The broadband light source 2 may be a diffuse light source, e.g. the broadband light source may have a spherical spatial light emission distribution, or may have a Lambertian spatial light emission distribution, e.g. such as the light emission distribution of a LED. For example, the broadband light source 2 may have a light emission divergence angle of at least 0.1 degrees, for instance of at least 0.2 degrees, e.g. of at least 0.5 degrees, or even higher, e.g. of 1 degree, 2 degrees or even more, e.g. up to 20 degrees.

The broadband light source 2 may be a relatively-inexpensive wideband light source, such as a light emitting diode (LED). In example embodiments, such an inexpensive light source can be used even though the etendue of such source when coupled into a single integrated waveguide would be unfavorable. In example embodiments of the present disclosure, an inexpensive and easily integrated light source can be used in an efficient and accurate absorption spectrum analysis device.

The device 1 further comprises a plurality of integrated optical waveguides 3 for guiding, e.g. for conducting, light. For example, the device may comprise an integrated photonics substrate 4, and the plurality of integrated optical waveguides 3 may be provided in or on this integrated photonics substrate 4. The plurality of integrated optical waveguides 3 may comprise a slab waveguide and/or a rib waveguide, e.g. a plurality of slab or rib waveguides provided in or on the integrated photonics substrate 4.

The number of integrated optical waveguides in the plurality of integrated optical waveguides 3 may be in the range of 100 to 10,000,000. The plurality of integrated optical waveguides 3 may comprise at least 100 integrated optical waveguides, e.g. at least 1000 integrated optical waveguides, or an even higher number of integrated optical waveguides, e.g. between 10,000 and 100,000, or even higher, e.g. between 100,000 and 10,000,000 integrated optical waveguides. For example, the number of integrated optical waveguides may be in the range of 1,000,000 and 5,000,000. The number of waveguides 3 may be determined depending on the etendue of the light emitted by the source 2 and to be coupled into the waveguides 3. For example, the etendue per waveguide may be of the order of 1 $\mu m^2$, while the etendue of the light emitted by the source 2, e.g. a LED, may be of the order of 1 $mm^2$. Therefore, in this example, a number of about 1,000,000 waveguides could be implemented in a device according to embodiments, such that the total etendue of the plurality of waveguides is of the same order of magnitude as the etendue of the light emitted by source 2. However, practical considerations such as maximum reticle size and cost of the device may be taken into account such as to reach a design balance between total achieved etendue and such other factors. The plurality of integrated optical waveguides 3 may be arranged substantially parallel, in a geometrical sense, in at least a light receiving portion where the light emitted by the broadband light source 2 is coupled into each of the plurality of integrated optical waveguides 3. For example, each integrated optical waveguide 3 may be adapted for guiding light in a longitudinal direction along the waveguide, the longitudinal directions of the waveguides being arranged substantially parallel in the light receiving portion. Thus, each waveguide of the plurality of integrated optical waveguides 3 may comprise a light receiving portion adapted for coupling the light into the waveguide, in which the light receiving portions of the plurality of integrated optical waveguides may be arranged substantially parallel with respect to each other.

The plurality of integrated optical waveguides 3 may be parallel waveguides, in a functional sense, e.g. the plurality of integrated optical waveguides 3 may be arranged and/or configured such as to prevent interaction, e.g. mixing, combining and/or splitting, of light travelling along different waveguides. Thus, each waveguide of the plurality of integrated optical waveguides 3 may be configured to keep the light travelling along different waveguides physically separate.

The device 1 further comprises a light coupler 10 for coupling the light emitted by the broadband light source 2 into the plurality of integrated optical waveguides 3. The light coupler 10 may comprise a collimator 11 for collimating the light emitted by the broadband light source 2 into a collimated radiation beam, and a beam shaper 12 for distributing the power of the collimated light over a discrete number of line shaped fields, each line shaped field being projected onto an light entry surface of a corresponding waveguide of the plurality of integrated optical waveguides 3. For example, the light entry surface of each waveguide may be a polished facet suitable for coupling light into the waveguide. In other embodiments, the light entry surface may be provided with a waveguide coupler, e.g. an integrated waveguide coupler, e.g. a grating coupler, to obtain a good coupling efficiency of the line shaped light field projected onto the entry surface to at least one light propagation mode of the waveguide.

At least part of the collimator 11 may for example have a parabolic shape, e.g. three-dimensional parabolic shape, a conic shape or horn-like shape.

In embodiments of the present disclosure, the beam shaper 12 may comprise a structured transparent slab, comprising a plurality of light separating lamellae, e.g. reflective lamellae for reflecting light away from the lamellae and generally toward the nearest line shaped light field, as schematically shown in FIG. 1.

Figure 3:
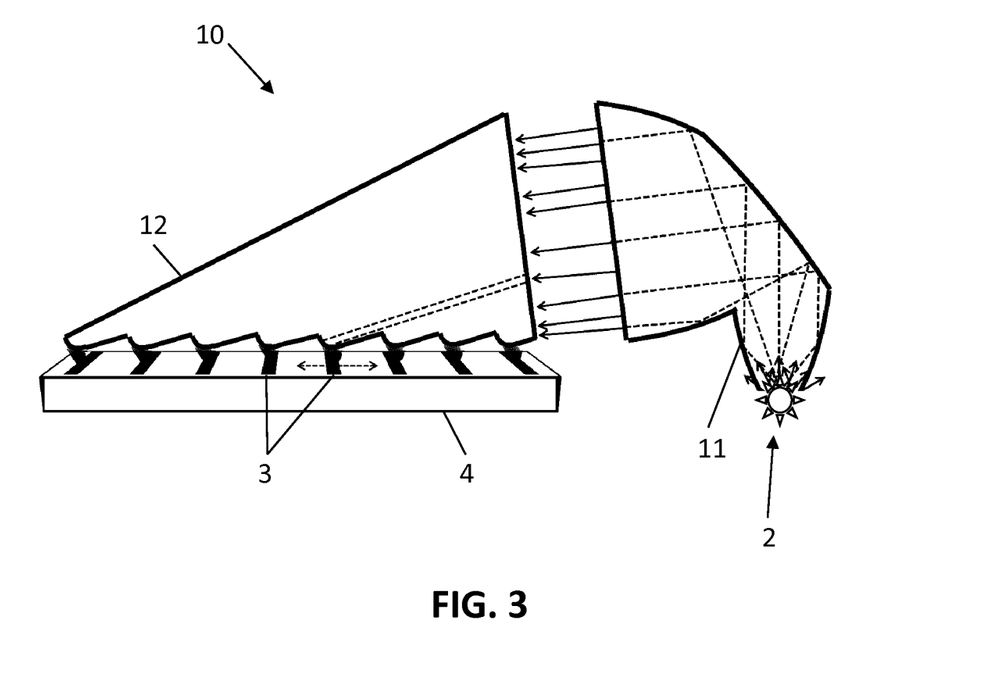
FIG. 3 shows a light coupler comprising a beam shaper and a collimator in a device according to embodiments of the present disclosure.

In embodiments of the present disclosure, the beam shaper 12 may have a wedge shape, e.g. as illustrated in FIG. 3. The collimator 11 and the beam shaper 12 may be arranged such that the beam shaper 12 can receive light from the collimator 11, e.g. via a wedge entrance area forming a short side of the wedge. The beam shaper 12 may be shaped such that light incident orthogonally at a wedge entrance area is guided directly to the wedge exit area without first being reflected at another surface of the wedge.

The beam shaper 12 may comprise an exit area for directing the light to the discrete number of line shaped fields, the exit area having a waved or stepped pattern, e.g. as shown in FIG. 3.

For example, the light coupler 10 may correspond to an optical radiation guiding system as disclosed in European patent application EP14157397.2, filed on 28 Feb. 2014 by IMEC vzw, and incorporated herein by reference. Specific features of the beam shaper and/or collimator disclosed in EP14157397.2 may be included in a device according to embodiments of the present disclosure for which protection is sought. Effects of such an optical radiation guiding system may contribute to solving a technical problem underlying the present disclosure.

The device 1 also comprises a microfluidic channel 5 for containing a fluid to be tested. For example, the microfluidic channel 5 may be formed in or on an integrated photonic substrate 4. For example, the microfluidic channel 5 may be adapted for containing a gas or a liquid, such as a biological fluid. The microfluidic channel 5 is arranged such as to allow an interaction of the light propagating through each of the integrated optical waveguides 3 with the fluid when contained in the microfluidic channel 5. The fluid to be tested may for example be introduced into the microfluidic channel 5, the microfluidic channel 5 having a portion that is arranged sufficiently close to each waveguide 3 such that an interaction of the light conducted in the waveguide can occur with the material in the microfluidic channel, e.g., but not limited thereto, an interaction of the evanescent field of the light.

The microfluidic channel 5 may comprise a micro-cuvette, and/or a reservoir for receiving the fluid to be tested. The microfluidic channel 5 may comprise a pump, e.g. an active means for transporting the fluid from a fluid receiving section, such as a reservoir or a micro-needle, through the channel, or may be adapted for passively transporting the fluid through channel, e.g. by means of capillary action, gravity and/or an externally applied pressure gradient.

The microfluidic channel 5 is arranged such as to allow an interaction of the light propagating through each of the integrated optical waveguides 3 with the fluid, when introduced into the microfluidic channel. For example, each of the integrated optical waveguides may have an interaction portion, e.g. a section of a substantial length, for example a respective waveguide section in an exposure zone 6, which is arranged in close proximity to the microfluidic channel 5, and thus close to the fluid under test when the device 1 is operational.

Each integrated optical waveguide 3 may be curved in an interaction portion where the light propagating through each of the integrated optical waveguides 3 can interact with the fluid when contained in the microfluidic channel 5. For example, this interaction portion of each waveguide 3 may be a section that is arranged in close proximity to the microfluidic channel 5.

The interaction portion may be a curved section 7 of the waveguide having an extrinsic curvature of at least the reciprocal of the diameter of the microfluidic channel 5. For example, the longitudinal axis of the waveguide 3, e.g. corresponding to the principal direction of light conduction in the waveguide, may have an extrinsic curvature, in the curved section 7, of at least the reciprocal of the diameter of the microfluidic channel 5.

Figure 2:
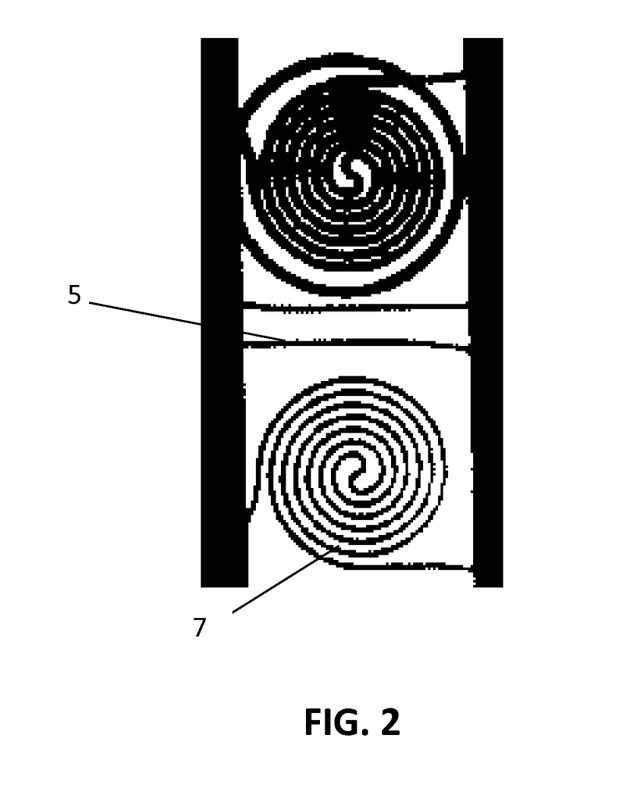
FIG. 2 shows waveguides having a spiral-like shape in an interaction portion thereof in a device according to embodiments of the present disclosure.

For example, as shown in FIG. 2, the waveguide 3 may have a spiral-like shape 7 in the interaction portion, e.g. in order to enable an interaction of the light propagating through the waveguide 3 with the fluid in the microfluidic channel 5 over a length of the waveguide 3 that is larger than the diameter of the microfluidic channel 5, e.g. that is at least 5 times larger, e.g. at least 10 times larger.

The device 1 also comprises a plurality of spectral analysis devices 8, e.g. optical spectrum analysis devices such as spectrometers. Each spectral analysis device 8 is optically coupled to a corresponding integrated optical waveguide 3 and adapted for receiving the light from the integrated optical waveguide 3 after interaction of the light with the fluid. Thus, each spectral analysis device 8 may be adapted for decomposing the broad light spectrum of the light after interaction with the sample into spectral components, e.g. the same plurality of spectral components, e.g. as defined by their peak wavelength and wavelength bandwidth, for each of the spectral analysis devices.

Each spectral analysis device 8 is further adapted for generating a signal, e.g. a plurality of signals, representative of a plurality of spectral components of the light. For example, the signal may be a digital signal or a plurality of analog electronic signals. The signal may be indicative of, e.g. proportional to, a number of photon counts in each of a plurality of wavelength ranges corresponding to the spectral components.

Each spectral analysis device 8 may for example comprise a spectrophotometer. Such spectrophotometer may comprise a refractive structure, such as a prism, or a diffractive structure, such as a diffractive grating to separate a plurality of spectral components of the light spectrum. The spectral analysis device 8 may comprise a scanning monochromator or a plurality of monochromators. The spectral analysis device 8 may comprise an interferometer, or a plurality of interferometers. For example, the spectral analysis device 8 may comprise an etalon. The spectral analysis device 8 may for example comprise a Fabry-Perot interferometer, a Michelson-Morley interferometer, a Twyman-Green interferometer, and/or a Mach-Zehnder interferometer.

The device 1 may also comprise a signal combiner 9, for combining signals, e.g. for performing an averaging or summing operation, adapted for receiving the signal from each of the spectral analysis devices 8 and for generating, e.g. for generating and outputting, an aggregate signal representative of the absorption spectrum of the fluid in the microfluidic channel 5.

The signal combiner 9 may for example comprise a processing unit, e.g. a processor, such as a general purpose processing unit, e.g. a central processing unit (CPU) or accelerated processing unit (APU), or an application specific integrated circuit (ASIC). The signal combiner may comprise an analog to digital converter. The signal combiner may comprise an arithmetic logic unit (ALU). The signal combiner may comprise an output unit for transmitting, e.g. by means of a communication bus and/or wireless communication module, a signal generated by the signal combiner to an external recipient. The signal combiner may comprise a data storage memory for storing a signal generated by the signal combiner.

The signal combiner 9 may furthermore be adapted for generating a signal indicative of a presence and/or a concentration of a predetermined target biological and/or chemical agent in the fluid. For example, the signal combiner 9 may output a signal indicative of a presence or concentration of a target analyte, or multiple predetermined target analytes, such as proteins, antigens, or antibodies. Thus, the device 1 may be adapted for use in environmental monitoring, toxicology, medical diagnostics, and/or gas sampling.

In a second aspect, the present disclosure also relates to a method for measuring an optical absorption property of a fluid as a function of wavelength. This method comprises emitting light using a broadband light source 2, and coupling the emitted light into a plurality of integrated optical waveguides 3 for guiding the light, e.g. using a light coupler 10. The emitted light is coupled into the plurality of integrated optical waveguides such that the light coupled into each integrated optical waveguide has substantially the same spectral distribution. The method further comprises bringing a fluid to be tested sufficiently close to each waveguide of the plurality of integrated optical waveguides 3 such as to allow an interaction of the light propagating through each waveguide with the fluid. For example, the method may comprise providing the fluid in a microfluidic channel 5 for containing the fluid that is arranged such as to allow an interaction of the light propagating through each waveguide with the fluid. The method further comprises analyzing the spectrum of the light after the interaction of the light with the fluid, e.g. using a plurality of spectral analysis devices 8 optically coupled to the corresponding integrated optical waveguides 3. Analyzing the spectrum may comprise decomposing the light received from each of the plurality of waveguides 3 after interaction with the fluid, into the same set of predetermined spectral components.

The method also comprises generating a signal representative of a plurality of spectral components of the light. A method according to embodiments of the present disclosure may be applied using a device according to embodiments of the first aspect of the disclosure. Further features of a method according to embodiments may be clear from the description of a corresponding device according to embodiments of the present provided hereinabove.

Generating the signal, e.g. a plurality of signals, representative of a plurality of spectral components of the light may comprise generating a digital signal or a plurality of analog electronic signals. The signal may be indicative of, e.g. proportional to, a number of photon counts in each of a plurality of wavelength ranges corresponding to the spectral components.

The method may be applied for obtaining colorimetric information pertaining to the fluid, e.g. for performing optical absorption measurements as function of wavelength, e.g. for determining an absorption spectrum of the fluid at a substantial spectral resolution, e.g. comprising determined values indicative of at least 32, e.g. at least 64, or even at least 128, such as at least 256, or even a higher number, e.g. 1000 or more, substantially distinct spectral components of the absorption spectrum. The method may be applied for detecting a biological and/or chemical agent in the sample being analyzed, e.g. for the detection of target analytes such as proteins, antigens, or antibodies. For example, the method may be used in environmental monitoring, toxicology, medical diagnostics, and/or gas sampling.

The method comprises emitting light using a broadband light source, such as an LED. Emitting the light may comprise emitting light having a predetermined light emission spectrum, e.g. a known and sufficiently stable spectrum suitable for use as a reference spectrum. Thus, a measurement of a spectrum of the light after having interacted with the fluid to be tested may be determined such that the measured spectrum is representative of absorption properties of the fluid, e.g. when compared to the known reference spectrum. Emitting the light may comprise emitting the light having a spherical spatial light emission distribution, or having a Lambertian spatial light emission distribution. For example, emitting the light may comprise emitting the light under a light emission divergence angle of at least 0.1 degrees, for instance of at least 0.2 degrees, e.g. of at least 0.5 degrees, or even higher, e.g. of 1 degree, 2 degrees or even more, e.g. up to 20 degrees.

The method also comprises coupling the emitted light into a plurality of integrated optical waveguides for guiding the light, e.g. using a light coupler. For example, the method may comprise guiding, e.g. conducting, the light in the plurality of integrated optical waveguides.

Coupling the emitted light into a plurality of integrated optical waveguides may comprise coupling the light into a plurality of substantially parallel light receiving portions of the plurality of integrated optical waveguides, e.g. parallel in a geometrical sense. Furthermore, coupling the emitted light into the plurality of integrated optical waveguides may comprise coupling the light into the plurality of parallel integrated optical waveguides, e.g. parallel in a functional sense. For example, the plurality of integrated optical waveguides may be arranged and/or configured such as to prevent interaction, e.g. mixing, combining and/or splitting, of light travelling along different waveguides. Thus, the method may also comprise keeping the light travelling along different waveguides physically separate.

Coupling the light into the plurality of integrated optical waveguides may comprise collimating the light emitted by the broadband light source into a collimated radiation beam, and distributing the power of the collimated light over a discrete number of line shaped fields. Each line shaped field may be projected onto a light entry surface of a corresponding waveguide of the plurality of integrated optical waveguides. For example, the light entry surface of each waveguide may be a polished facet suitable for coupling light into the waveguide. In other embodiments, the light entry surface may be provided with a waveguide coupler, e.g. an integrated waveguide coupler, e.g. a grating coupler, to obtain a good coupling efficiency of the line shaped light field projected onto the entry surface to at least one light propagation mode of the waveguide.

Distributing the power of the collimated light over the discrete number of line shaped fields may comprise projecting the collimated light through a structure comprising a plurality of light separating lamellae, e.g. reflective lamellae for reflecting light away from the lamellae and generally toward the nearest line shaped light field.

The method comprises bringing a fluid to be tested sufficiently close to each waveguide of the plurality of integrated optical waveguides such as to allow an interaction of the light propagating through each waveguide with the fluid. For example, the method may comprise providing the fluid in a microfluidic channel for containing the fluid, the microfluidic channel being arranged such as to allow an interaction of the light propagating through each waveguide with the fluid. The method may comprise actively transporting, e.g. pumping, the fluid from a fluid receiving section, such as a reservoir or a micro-needle, through the channel. The method may comprise passively transporting the fluid through the microfluidic channel, e.g. by means of capillary action, gravity, and/or an externally applied pressure gradient.

Bringing the fluid to be tested sufficiently close to each waveguide of the plurality of integrated optical waveguides such as to allow an interaction of the light propagating through each waveguide with the fluid may comprise guiding, e.g. conducting, the light in each waveguide through a waveguide section that is close to the fluid under test over a substantial length, e.g. a curved section of the waveguide, such as a curved section having an extrinsic curvature of at least the reciprocal of the diameter of the microfluidic channel. For example, bringing the fluid sufficiently close to each waveguide may comprise guiding, e.g. conducting, the light is each waveguide along a spiral-like path near the fluid, e.g. in order to enable an interaction of the light propagating through the waveguide with the fluid in the microfluidic channel over a length of the waveguide that is larger than the diameter of the microfluidic channel, e.g. that is at least 5 times larger, e.g. at least 10 times larger.

The method may also comprise combining generated signals, e.g. for performing an averaging or summing operation. For example, this combining may comprise receiving signals, e.g. from each of a plurality of spectral analysis devices, and generating, e.g. generating and outputting, an aggregate signal representative of the absorption spectrum of the fluid. The method may thus, for example, comprise generating a signal indicative of a presence and/or a concentration of a predetermined target biological and/or chemical agent in the fluid. For example, the step of combining may comprise outputting a signal indicative of a presence or concentration of a target analyte, or multiple predetermined target analytes, such as proteins, antigens or antibodies.

For example, a method in accordance with embodiments of the present disclosure may be used in environmental monitoring, toxicology, medical diagnostics and/or gas sampling.

In a further aspect, the present disclosure may also relate to the use of a device 1 according to embodiments of the present disclosure for the detection and/or quantification of biological and/or chemical agents in the fluid. The present disclosure may also relate to the use of a device according to embodiments of the present disclosure for the detection and/or quantification of target analytes such as proteins, antigens or antibodies. The present disclosure may also relate to the use of a device according to embodiments of the present disclosure for environmental monitoring, toxicology, medical diagnostics and/or gas sampling.

The invention claimed is:

1. A device for measuring an optical absorption property of a fluid as a function of
wavelength, the device comprising:
a broadband light source for emitting light;
a plurality of integrated optical waveguides for guiding the light, the waveguides being arranged to prevent interaction of light travelling along different waveguides;
a light coupler for coupling the light emitted by the broadband light source into the plurality of integrated optical waveguides such that the light coupled into each of the integrated optical waveguides has substantially a same spectral distribution;
a microfluidic channel for containing the fluid, the microfluidic channel being arranged to allow an interaction of the light propagating through each of the integrated optical waveguides with the fluid when contained in the microfluidic channel; and
a plurality of spectral analysis devices,
wherein each spectral analysis device is optically coupled to a corresponding integrated optical waveguide to receive the light after the interaction of the light with the fluid,
wherein at least one integrated optical waveguide of the plurality of integrated optical waveguides comprises an interaction portion, wherein the light propagating through the integrated optical waveguides interacts with the fluid when contained in the microfluidic channel at the interaction portion, wherein the interaction portion comprises a curved section that is curved with respect to a longitudinal axis of the waveguides, the longitudinal axis corresponding to a principal direction of light conduction in the waveguides, wherein the curved section has an extrinsic curvature of at least a reciprocal of the diameter of the microfluidic channel, and
wherein each spectral analysis device is adapted for generating a signal representative of a plurality of predetermined spectral components of the light.

2. The device according to claim 1, wherein the light coupler comprises:
a collimator for collimating the light emitted by the broadband light source into a collimated radiation beam; and
a beam shaper for distributing power of the collimated light over a discrete number of line shaped light fields, wherein the beam shaper is arranged such that each line shaped light field is projected onto a light entry surface of a corresponding integrated optical waveguide of the plurality of integrated optical waveguides.

3. The device according to claim 2, wherein the collimator has a parabolic shape, a conic shape, or a horn-like shape.

4. The device according to claim 2, wherein the beam shaper comprises a structured transparent slab comprising a plurality of light separating lamellae for reflecting light away from the light separating lamellae and toward a nearest line shaped light field.

5. The device according to claim 2, wherein the beam shaper has a wedge shape, and wherein the collimator and the beam shaper are arranged such that the beam shaper can receive light from the collimator via a wedge entrance area forming a short side of the wedge shape.

6. The device according to claim 1, wherein the number of integrated optical waveguides in the plurality of integrated optical waveguides is in a range of 100 to 10,000,000.

7. The device according to claim 1, wherein each integrated optical waveguide of the plurality of integrated optical waveguides comprises a light receiving portion adapted for coupling the light emitted by the broadband light source into the integrated optical waveguide, and wherein the light receiving portions of the plurality of integrated optical waveguides are arranged substantially parallel with respect to each other.

8. The device according to claim 1, wherein each integrated optical waveguide of the plurality of integrated optical waveguides is configured to keep the light travelling along different waveguides physically separate.

9. The device according to claim 1, wherein at least one integrated optical waveguide of the plurality of integrated optical waveguides has a spiral-like shape in the interaction portion.

10. The device according to claim 1, wherein the broadband light source has a substantially spherical or Lambertian spatial light emission distribution.

11. The device according to claim 10, wherein the broadband light source comprises a light emitting diode.

12. The device according to claim 10, further comprising a signal combiner adapted for receiving the signal from the plurality of spectral analysis devices and for generating therefrom an aggregated signal representative of an absorption spectrum of the fluid.

13. The device according to claim 12, wherein the signal combiner is further adapted for generating a signal indicative of a presence and/or a concentration of a predetermined target biological and/or chemical agent in the fluid.

14. A method for measuring an optical absorption property of a fluid as a function of wavelength, comprising:
emitting light using a broadband light source;
coupling the emitted light into a plurality of integrated optical waveguides for guiding the light, wherein the waveguides are arranged to prevent interaction of light travelling along different waveguides, and wherein the light coupled into each of the integrated optical waveguides has substantially the same spectral distribution, and
providing the fluid in a microfluidic channel for containing the fluid that is arranged such as to allow an interaction of the light propagating through each integrated optical waveguide with the fluid, wherein at least one integrated optical waveguide of the plurality of integrated optical waveguides comprises an interaction portion, wherein the light propagating through the integrated optical waveguides interacts with the fluid when contained in the microfluidic channel at the interaction portion, wherein the interaction portion comprises a curved section that is curved with respect to a longitudinal axis of the waveguides, the longitudinal axis corresponding to a principal direction of light conduction in the waveguides, wherein the curved section has an extrinsic curvature of at least a reciprocal of the diameter of the microfluidic channel.

15. The method of claim 14, further comprising bringing a fluid to be tested sufficiently close to each integrated optical waveguide of the plurality of integrated optical waveguides such as to allow an interaction of the light propagating through each integrated optical waveguide with the fluid.

16. The method of claim 15, further comprising analyzing a spectrum of the light after the interaction of the light with the fluid.

17. The method of claim 14, further comprising generating a signal representative of a plurality of spectral components of the light.

18. The device according to claim 1, wherein the interaction portion has a length that is larger than the diameter of the microfluidic channel.

19. The device according to claim 18, wherein the interaction portion has a length that is at least 5 times larger than the diameter of the microfluidic channel.

20. The device according to claim 1, wherein the broadband light source has a light emission divergence angle of at least 0.2 degrees.

21. The device according to claim 20, wherein the broadband light source has a light emission divergence angle of 1 degree.

* * * * *